(12) United States Patent
Hasegawa et al.

(10) Patent No.: US 7,288,948 B2
(45) Date of Patent: Oct. 30, 2007

(54) PATTERNED WAFER INSPECTION METHOD AND APPARATUS THEREFOR

(75) Inventors: Masaki Hasegawa, Sayama (JP); Hisaya Murakoshi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/016,990

(22) Filed: Dec. 21, 2004

(65) Prior Publication Data

US 2005/0139772 A1    Jun. 30, 2005

(30) Foreign Application Priority Data

Dec. 24, 2003    (JP)   ............... 2003-426171

(51) Int. Cl.
*G01R 31/305* (2006.01)

(52) U.S. Cl. ...................................... 324/751

(58) Field of Classification Search ............... 324/751, 324/765, 158.1, 750; 250/310, 311
See application file for complete search history.

(56) References Cited

U.S. PATENT DOCUMENTS

| | | | | |
|---|---|---|---|---|
| 5,521,517 | A * | 5/1996 | Shida et al. | 324/751 |
| 6,091,249 | A * | 7/2000 | Talbot et al. | 324/751 |
| 6,559,663 | B2 * | 5/2003 | Shinada et al. | 324/751 |
| 6,567,168 | B2 * | 5/2003 | Nara et al. | 356/394 |
| 6,614,244 | B2 * | 9/2003 | Yamada et al. | 324/751 |

FOREIGN PATENT DOCUMENTS

| | | |
|---|---|---|
| JP | 05-258703 | 10/1993 |
| JP | 2000-286310 | 10/2000 |
| JP | 2003-202217 | 7/2003 |
| JP | 2004-151119 | 5/2004 |

OTHER PUBLICATIONS

Low Energy Electron Microscopy, IBM J. Res. Develop. vol. 44, No. 4, Jul. 2000, by RmM. Tromp.
Imaging Hot-Electron Emission From Metal-Oxide Semiconductor Structures, Mankos, Physical Review Letters, vol. 76, No. 17 (Nov. 9, 1995).

* cited by examiner

*Primary Examiner*—Ha Tran Nguyen
*Assistant Examiner*—Tung X. Nguyen
(74) *Attorney, Agent, or Firm*—Antonelli, Terry, Stout & Kraus, LLP.

(57) ABSTRACT

A defect inspection apparatus is provided which allows a technology for inspecting a pattern on a wafer by using an electron beam to implement a high-resolution and higher-speed inspection. A semiconductor wafer is irradiated with an electron beam and electrons reflected in the vicinity of the wafer are detected. The presence or absence of a defect and the location thereof are measured by forming an image from only a component which changes with a periodicity larger than a size of a circuit pattern or the repetition periodicity thereof by using lenses and comparing an image signal with a preset value. Since only the component which changes with a periodicity larger than the size of the circuit pattern with a surface potential distortion and the repetition periodicity thereof is observed with a resolution lower than required to observe the pattern itself instead of detecting a defect through a comparison between extremely small pattern images, an inspection throughput can be increased exponentially compared with that of a conventional SEM inspection.

14 Claims, 7 Drawing Sheets

US 7,288,948 B2

PATTERNED WAFER INSPECTION METHOD AND APPARATUS THEREFOR

CLAIM OF PRIORITY

The present application claims priority from Japanese Application JP 2003-426171 filed on Dec. 24, 2003, the content of which is hereby incorporated by reference into this application.

FIELD OF THE INVENTION

The present invention relates to a method and apparatus for inspecting an electric defect in an extremely small circuit formed on a semiconductor wafer.

BACKGROUND OF THE INVENTION

For the inspection of a defect present in a circuit pattern formed on wafers in a process of manufacturing a semiconductor device, there have been an optical inspection method and an inspection method using a SEM system.

In accordance with the optical inspection method, an image of a surface of a wafer is optically sensed and a defective portion is specified through the analysis of the image. This enables the defect inspection of the wafer surface to be performed at an extremely high speed.

In accordance with the SEM inspection method, a defect present in a circuit pattern is detected by scanning a surface of a wafer formed with a circuit pattern with an electron beam focused onto a spot and comparatively inspecting obtained SEM images. By using the SEM defect inspection of a circuit pattern, extremely small etching residues and pattern defects which are not more than the resolution of an optical microscope and electric defects such as faulty openings of extremely small connection holes can be detected. A technology for comparatively inspecting a pattern by using such a SEM system is disclosed in, e.g., a Japanese Laid-Open Patent No. H 05(1993)-258703.

Although the SEM inspection method has an advantage of allowing the detection of an electric defect over the optical inspection method, however, it has a disadvantage of an significantly lower inspection speed compared to the optical pattern inspection method.

In addition, the SEM inspection requires extremely high-speed obtention of the image of the circuit pattern to achieve a practical inspection speed so that it is necessary to form the image with a sufficient S/N ratio under short-term beam irradiation. Accordingly, it is necessary to adjust the current value of an electron beam for irradiating the wafer to about 10 nA or more, which is 100 times or more larger than the value of a beam current used in a normal scanning electron microscope.

SUMMARY OF THE INVENTION

As described above, the SEM defect detection technology has the drawback of a low throughput (inspection speed or yield of inspection). Moreover, improvement for achieving higher inspection speed has certain limitation, as described herein below.

To improve the throughput of a SEM system, the current density of an electron beam applied for irradiation should be increased with a view to holding the quality (e.g., the S/N ratio) of a sensed image at an inspectable level. In a current situation also, the current density of the electron beam has been adjusted to be considerably higher than in the normal SEM but an increase in current density is limited due to the brightness of an electron source, a spatial charge effect, or the like.

To increase the resolution of a SEM, it is necessary to reduce the spot size of the irradiation electron beam. However, the current density of the electron beam and the spot size are under trade-off relationship therebetween. For example, when a resolution of about 0.1 μm is to be obtained, an electron beam current reaches a theoretical limit at about several hundreds of nanoamperes and is about 100 nA in an actual situation.

To guarantee sufficient signal-to-noise ratio that allows meaningful execution of image processing when the beam current value is 100 nA and the resolution is 0.1 μm, the time required to inspect the surface region of a sample having an area of 1 cm² cannot be reduced to a period shorter than 100 sec.

Furthermore, in a SEM inspection apparatus that utilizes secondary electrons for image formation, factors of widely spread emission angle distribution of secondary electron and widely spread energy distribution of the secondary electron expanding in a range as much as from 1 to 10 eV cause a reason to reduce inspection sensitivity. The resolution when a voltage of −5 kV is applied to the sample is about 0.2 μm. In addition, not all of emitted secondary electrons are contributed for image formation. According to the calculation in the Japanese laid-open patent, e.g., only the secondary electrons within the emission angle ranging over 1.1 mrad or less at an image plane after passing through an objective lens are contributed for image formation. The ratio of the secondary electrons with the above-identified emission angle to whole secondary electrons generated by the irradiation of primary electron beam is at most about 10%. Moreover, although the calculation in the Japanese laid-open patent has been performed on the assumption that the energy width of the emitted secondary electrons contributed for the image formation is 1 eV, actual energy width of the distribution of the emitted secondary electrons is several electron volts or more. Particularly, tail in the energy distribution at higher energy side stretches to fairly high energy level, such as 50 eV or so. Since only the secondary electrons having energy with the energy width of at most 1 eV of the wide energy distribution should be extracted, the number of secondary electrons contributing for image formation is further reduced to a fraction of the number of the extracted secondary electrons.

It is therefore an object of the present invention to provide a defect inspection method and a defect inspection apparatus that allow high-sensitivity and high-speed detection of an electrically defective portion in a circuit pattern having defects by irradiating an inspection target with a charged particle beam such as an electron beam or an ion beam.

The object of the present invention is attainable by sensing an image by intentionally lowering the resolution. As a result of a research, the present inventors have found that mere specification of an electric defect does not need an image with a high resolution. A detailed description will be given herein below with reference to the drawings.

FIG. 3 shows an equipotential line 305 in the vicinity of the surface of a sample wafer which was obtained as a result of a numerical value simulation. A cross-sectional portion 304 of a pattern has conductive material portions 302 (hollow portions) each of the size of 70 nm and insulating film portions 301 (hatched portions). It was assumed that, of the conductive material portions, only the center one was at −1 V and the other conductive material portions were at 0 V. Although FIG. 3 shows only a part of the sample, the conductive material portions 302 and the insulating film portions 301 actually expand on both sides of FIG. 3 in various cycles in accordance with a circuit pattern. FIG. 3 shows an assumed case where the connection between only the center one of the conductive material portions and a substrate is insufficient so that the center conductive material portion has been negatively charged by 1 V compared with the other conductive material portions on both sides thereof. It was assumed that the insulator portion had been charged to −2 V. The drawing shows a transition in which the disturbed equipotential lines formed by the pattern having the different potential at the center thereof are changed into a distribution having a mild peak over the defect as extremely small fluctuations are reduced with distance from the surface of the sample. It is to be noted that the range in which the potential is disturbed in the vicinity of the electric defect becomes larger in size than the pattern with distance from the surface of the sample to have an expansion approximately triple the pattern size in this drawing.

To specify the presence or absence of an electric defect and the location thereof, therefore, it is unnecessary to form an image of a circuit pattern and sufficient to form an image of a distortion in a potential distribution which is larger than the pattern size. In other words, an electric defect in an extremely fine pattern can be detected even when the resolution of an electro-optical system for defect detection is lowered. When the resolution of the electro-optical system is lowered, the pattern does not distinctively appear in the image and only the portion with a potential distortion resulting from an electric defect or the like appears as the image. Consequently, a defect can be detected appropriately only by detecting the presence of the image, which is different from the conventional pattern comparison. Specifically, a threshold value is set preliminarily and a defect can be determined based on magnitude relative to the set value.

In addition, the use of the foregoing method allows a reduction in the number of the pixels of an image detector, i.e., a reduction in image data. Since the detection is performed not by a comparison between pattern images which requires image processing but by a magnitude comparison with the set value, a defect detection process can be simplified. As a result, it becomes possible to reduce a burden on an image processing mechanism such as an engine for image processing and significantly increase the speed of defect detection.

According to the present invention, an inspection method and an inspection apparatus can be implemented which allow, by using an electron beam, high-sensitivity and high-speed inspection of an extremely small opening or an electric defect such as a short circuit or a leakage current in the surface of a sample such as a semiconductor device.

DESCRIPTION OF THE PREFERRED EMBODIMENTS

Figure 1:
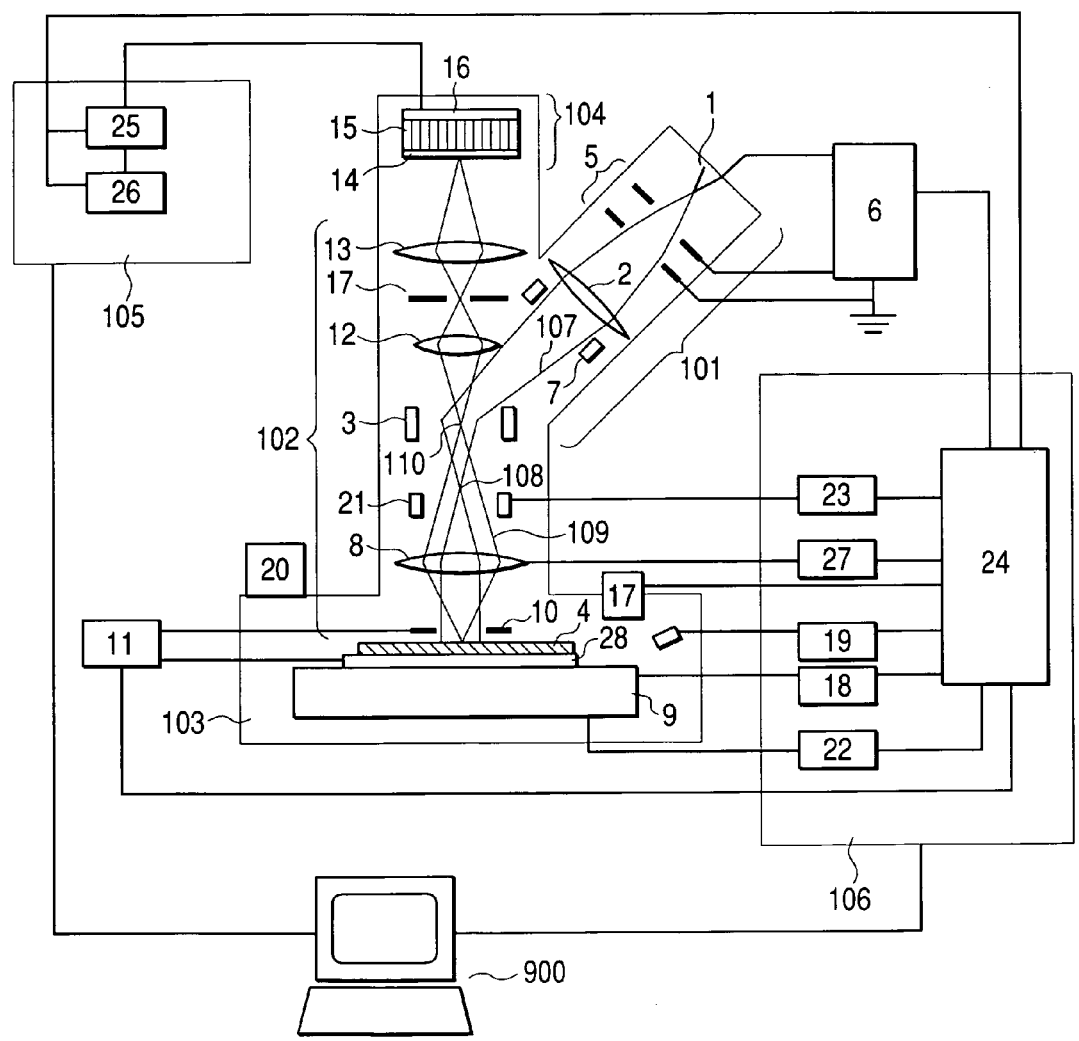
FIG. 1 is a view showing a schematic structure of an inspection apparatus as a first embodiment of the present invention.

Referring to the drawings, a structure of an embodiment of the present invention will be described herein below in detail.

Embodiment 1

In the present embodiment, a description will be given to an example in which the present invention is applied to a defect inspection apparatus of a mirror projection (MPJ) type. The description will be given first to the principle of the MPJ and a problem to be solved.

A consideration will be given to a situation in which the plurality of target regions (areal regions) of a surface of a sample are irradiated with a planar electron beam having a two-dimensional expansion and a negative potential is further applied to a wafer. The negative potential is adjusted to such a value as to return a major part of the electron beam in the vicinity of the outermost surface of the wafer. Specifically, the negative potential is adjusted to a level higher by 0.5 V to 5 V than a potential at an electron source. At this time, the irradiation beam is reflected immediately before the sample and returned by an electric field without colliding with the sample. The electrons will be termed "returned electrons" or "mirror electrons" herein below.

Figure 2:
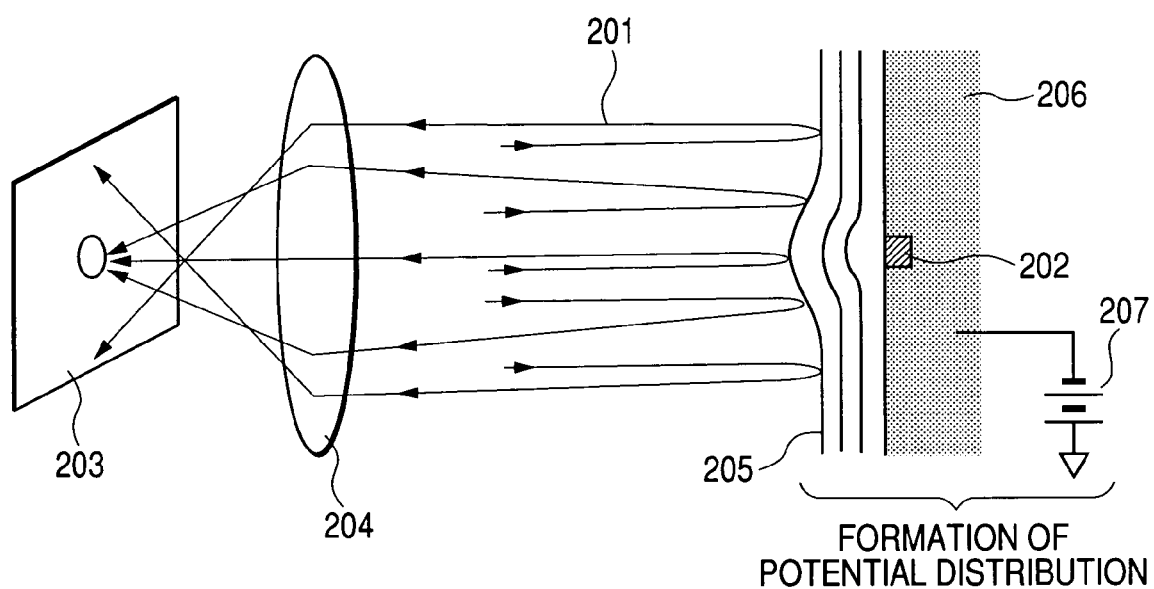
FIG. 2 is a view for illustrating the principle of the present invention.
Figure 3:
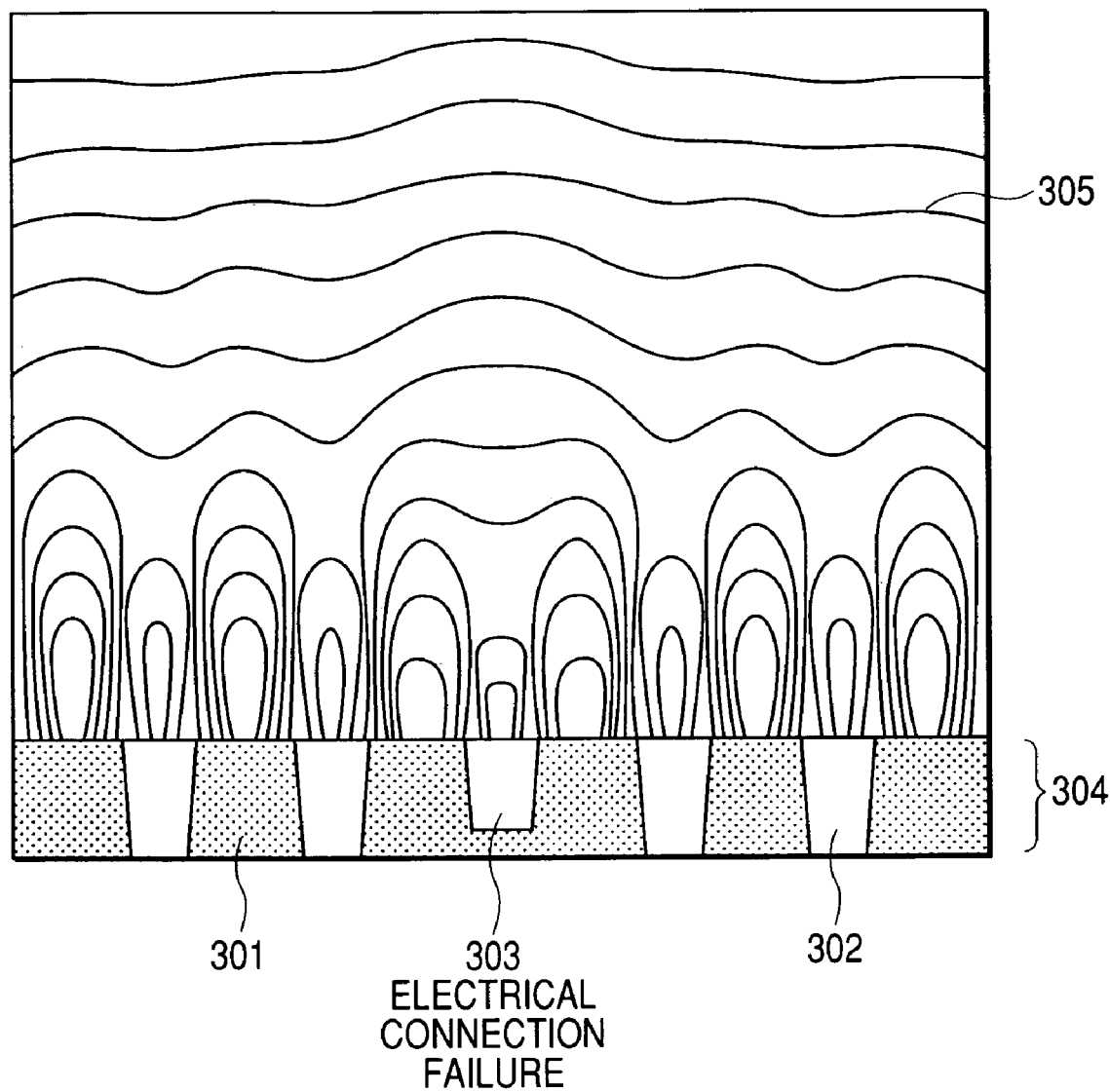
FIG. 3 is a view for illustrating the principle of the present invention.

FIG. 2 diagrammatically shows an electron beam 201 which is incident in perpendicular relation to an equipotential line 205 in the vicinity of the outermost surface of a wafer 7 and returned as mirror electrons. Due to a defect 202 present in the surface of the wafer 7, the equipotential line 205 has a non-uniform configuration at the position where the defect is present. The electron beam incident perpendicularly thereon is not returned perpendicularly thereby but is returned at an angle as shown in the drawing to be incident on a lens 204. The lens 204 is a schematic representation of the operation of an objective lens and an image forming lens in an actual image forming optical system using a single equivalent lens. It can be seen from FIG. 2 that, when an image is formed on an image plane 203 by using the lens, the electron beam from the portion with the defect 202 is focused onto one portion of the image plane and the portion becomes brighter than the surrounding portion. The resulting images allow the detection of the presence of the electric defect and the location of the defect. Since an MPJ system allows simultaneous irradiation with an electron beam larger in current than in a SEM system and simultaneous acquisition of images, it is expected to enable ultra-high-speed formation of images compared with the SEM system.

Even though it is attempted to simultaneously form images by enlarging a region irradiated with the electron beam and applying a large current as a planar beam for irradiation, not all of electrons applied for irradiation are reflected as mirror electrons and not all of the generated mirror electrons contribute to image formation. According to an experiment, the quantity of emitted mirror electrons is smaller than the quantity of electrons in an irradiation beam current by two orders of magnitude. Because of a low proportion of the electrons contributing to image formation, it is difficult to form an image having a required S/N ratio and provide compatibility between a high resolution and a high-speed inspection. As a result, an inspection time has not been reduced as expected in a conventional defect inspection apparatus using a MPJ system. The present embodiment has been achieved in view of such a fact and it is therefore an object of the present embodiment to significantly improve the throughput of an MPJ inspection apparatus.

Next, a structure of an inspection apparatus as the embodiment of the present invention is shown in FIG. 1. The apparatus is roughly composed of an electron beam irradiation system 101, a mirror electron image forming optical system 102, a sample room 103, an image detection unit 104, an image processor 105, and a control unit 106. In the drawing, however, the depiction of a pump for vacuum exhaust, a controller thereof, exhaust system piping, and the like is omitted. A computer 900 comprises an input mechanism for setting and inputting control parameters for the image processor 105 and the control unit 106 and a display. The electron beam irradiation system 101 has, e.g., an electron gun 1, a condenser lens 2, an E×B deflector 3, and a mechanism for rendering beams parallel as main components. In the present embodiment, an objective lens 8 is used as the mechanism for rendering beams parallel. There may be cases where various other extra components are provided, but the description thereof will be omitted. The mirror electron image forming optical system 102 has a circular hole electrode 10, the objective lens 8, the E×B deflector 3, and lenses 12 and 13 as main components. There may also be cases where the mirror electron image forming optical system 102 has other various extra components, but the detailed description thereof will be omitted.

In the electron beam irradiation system 101, an irradiation electron beam 107 emitted from the electron source 1 is converged by the condenser lens 2 and deflected by the E×B deflector 3 to form a cross over 108. The converged electron beam 107 is then changed into parallel fluxes by the objective lens 8 and applied to a surface of a sample wafer 4 for irradiation. As the electron source 1, a Zr/O/W Schottky electron source was used. This allows stable formation of a large-current beam (e.g., 1.5 μA) with an energy width of 1.5 eV or less. An extraction voltage to the electron source and an acceleration voltage to an extracted electron beam are supplied from a high voltage controller 6 to an extraction electron system 5 so that the extraction voltage and the acceleration voltage are adjustable. As will be described later, the E×B deflector 3 functioning as a beam separator is located in the vicinity of an image plane 110 for an image forming electron beam 109. At this location, however, the E×B deflector 3 causes the aberration of the irradiation electron beam 107. To correct the aberration, an arrangement has been adopted in which another E×B deflector 7 for aberration correction is disposed between the irradiation-system condenser lens 2 and the E×B deflector 3.

Although the irradiation electron beam 107 is deflected by the E×B deflector 3 to have an optical axis perpendicular to the wafer 4, the E×B deflector 3 has a deflecting effect only on an electron beam in a direction from the electron beam source toward the sample so that it functions as the beam separator. Since the irradiation electron beam 107 deflected by the E×B deflector 3 is changed into the parallel flux by the objective lens 8, it becomes a so-called "blanket beam" irradiating a region having a large expansion of several to several tens of micrometers without forming, on the sample, an extremely small irradiation spot of several to several tens of nanometers as is formed by a SEM. Because a deflective aberration caused by the separator E×B deflector 3 is corrected by the E×B deflector 7, the extremely small cross over 108 is formed on the focal plane of the objective lens 8 to allow the irradiation of the sample wafer 4 with the irradiation electron beam 107 with excellent parallelness.

The surface region of the sample wafer 4 to be irradiated with the irradiation electron beam 107 is intended to have a large area of, e.g., 50 μm×50 μm or 100 μm×20 μm by adjusting the power of the condenser lens 2 (e.g., a quantity of a current in a coil in the case of a magnetic field lens). The power of the condenser lens 2 may be either adjusted manually by the user of the apparatus or controlled automatically by causing the computer 900 to control the voltage from the voltage source applied to the condenser lens. In that case, the user of the apparatus effects the automatic control of the condenser lens by, e.g., inputting the size of the planar beam to the computer 900 and adjusting the power source voltage to a level commensurate with the size.

The circular hole electrode 10 has been disposed in the vicinity of the sample wafer 4 placed on a sample moving stage 9 in the sample room 103 and a negative potential substantially equal to or slightly higher (larger in absolute value) than the acceleration voltage for the electron beam has been applied between the circular hole electrode 10 and the sample wafer 4 by a sample application power source 11. The irradiation electron beam 107 is decelerated before the wafer 4, reflected, and returned as mirror electrons in an upward direction by the negative potential. It has already been described that the mirror electrons reflect information on the electric defect in the circuit pattern on the wafer 4. The mirror electrons receive a converging effect by the objective lens 8 and move vertically upward since the E×B deflector 3 does not have the deflecting effect on the electron beam that has moved from below so that an image projected by the objective lens 8, the middle lens 12, and the projection lens 13 is converted to an electric signal by the image detection unit 104.

The image detection unit 104 is composed of a scintillator 14, an optical image transmitter 15, and an optical image detector 16 and an image is projected thereon in enlarged relation. A contrast aperture 13 can also be inserted on an electron diffraction image formed by the objective lens 8 or the middle lens 12 to perform such an adjustment operation as to emphasize only a defective portion by adjusting the contrast of the image and eliminating an image of a normal pattern. The distribution of local charged potentials over the surface of the wafer, i.e., an electric defect image fetched by the image detection system 104 is sent to the image processor 105.

In accordance with the present invention, there is no collision of the electron beam with the wafer 4 so that the sample wafer is not charged normally. However, since the sample wafer should be charged for the detection of an electric defect, a charging controller 17 has been provided. The charging controller comprises an electron source using an electron source composed of carbon nanotubes tied in a bundle, a tungsten filament thermo-electron source, an $LaB_6$ electron source, or the like to emit a large-current electron beam from a surface having a certain extent of area (several hundreds of micrometers to several tens of millimeters). To control the charged state of the wafer, it is necessary to adjust the incident energy of an electron beam for charging with respect to the wafer so that an electrode for this purpose or the like is provided. For the current value of the electron beam for charging and the incident energy thereof, optimum conditions for a defect inspection can be given by the control unit 106.

Although the present embodiment has shown the structure using the electron beam as the charge controller, light ranging in wavelength from an ultraviolet ray to a soft X-ray may also be used as a mechanism for charging the sample wafer instead of the electron beam. In the case of using light as the charging mechanism, the light is not in the least affected by the electro-optical system or by the wafer potential, which enables simultaneous observation during a defect inspection and charging control effected by light beam irradiation.

As a mechanism for causing charging simultaneously with microscopic observation during a defect inspection, the energy distribution of the irradiation electron beam 107 may also be used instead of the foregoing method using light. The energy distribution of electrons generated from the electron source 1 has a peaked configuration in which the energy initially has an expansion of about 1.5 eV or less. In view of this, the voltage applied from the power source 11 to the circular hole electrode 11 and to the sample wafer 4 is controlled to set the sample potential which reflects the irradiation electron beam 107 within the peak of the energy distribution of the irradiation electron beam. A group of electrons having energy higher than the set potential value surpass the sample potential to be incident upon the sample wafer.

On the other hand, a group of electrons having energy lower than the set potential are repelled to contribute to image formation as mirror electrons. The sample is negatively charged with the electrons incident on the sample. A negative potential newly formed at the time of the injection of a fixed quantity of electrons reflects all of the incident electrons so that the injection of the electrons is automatically stopped. If some of the electrons injected into the sample are released therefrom, the amount of charging is reduced and the negative potential resulting from charging is reduced. As a result, incident electrons are injected again into the sample to compensate for the reduction in the amount of charging so that the amount of charging is always held constant. Accordingly, if the voltage from the power source 11 is set such that the sample potential is included in the peak of the energy distribution of the irradiation electron beam, charging can be performed simultaneously with observation without using the charging controller 17. The set potential for the initial injection of electrons is adjusted by shifting the voltage from the power source 11 slightly in a positive direction relative to the acceleration voltage supplied from the power source 6. The amount of shifting should be smaller than the width of the energy distribution of incident electrons. An optimum amount of shifting differs depending on the material of the sample.

If a proper value has been measured preliminarily for each material and tabulated, therefore, the system is allowed to set a proper amount of shifting based on a table through the mere selection of conditions associated with the material by the user. The table can be stored in, e.g., the control unit 106 or the computer 900. It is also possible for the user to perform adjustment. The adjustment is performed through the control unit 106 for controlling each of the power sources 6 and 11.

Figure 4:
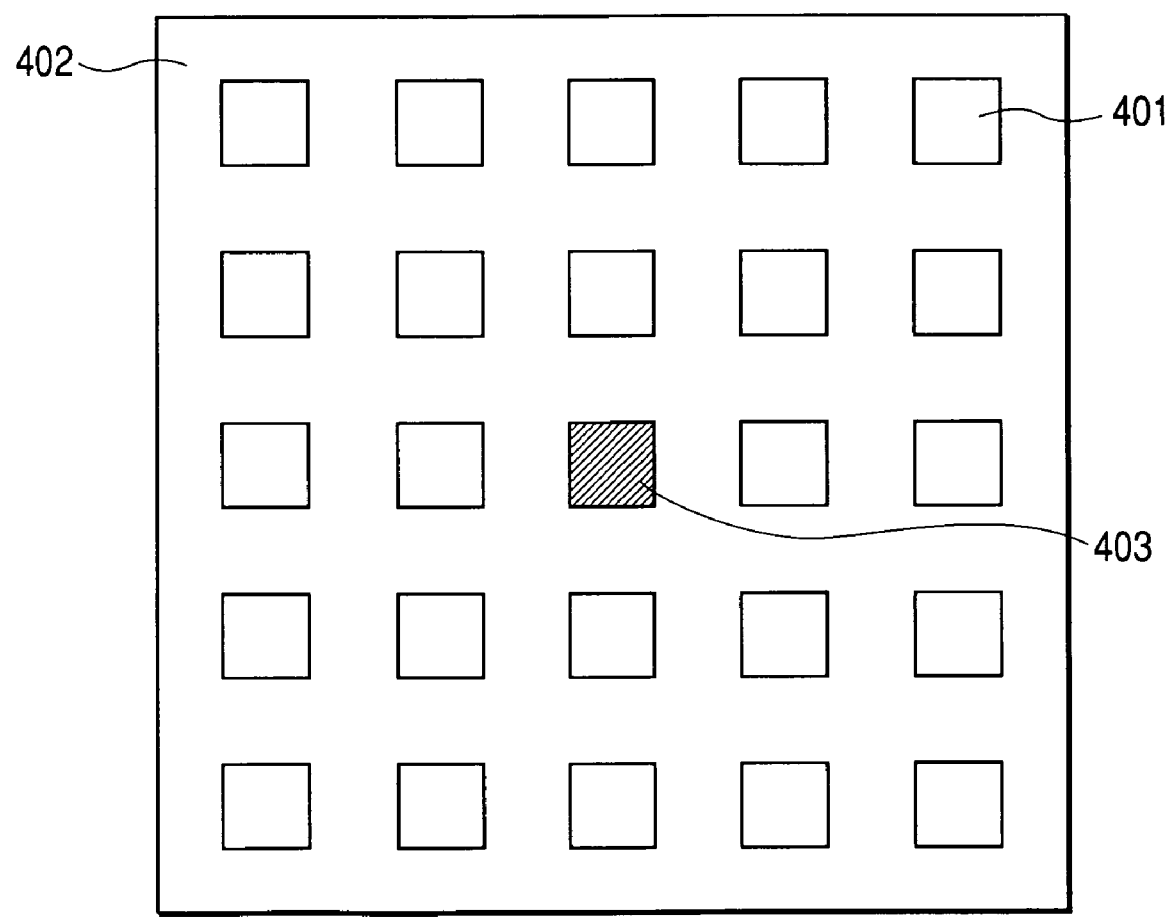
FIG. 4 is a view for illustrating a model pattern for comparing the states of images formed by mirror electrons.

To obtain an image in which only a defect on the sample wafer is emphasized, it is necessary to adjust optical conditions for the irradiation optical system 101 and the image forming optical system 102. A description will be given first to what kind of adjustment should be performed by using the result of simulating image forming characteristics in the optical system of the present embodiment. A consideration will be given to a model in which rectangular patterns 401 having sides of 70 nm are arranged in a 5×5 configuration as shown in FIG. 4. These rectangular patterns represent a model of vias connecting upper-layer and lower-layer wirings. An insulating film 402 is interposed between the individual rectangles. These rectangular patterns are normally connected to the lower-layer wiring, except for the rectangular pattern 403 at the center which is not connected and is electrically insulated.

In this case, if a charging process as performed by using the charging controller 17 shown above or the like is performed, the insulating film 402 and the defective center pattern 403 are charged to form potentials, while the other normal patterns 401 connected to the lower-layer wiring remain at 0 V. It was assumed in the following simulation that the normal patterns were at 0 V, the potential of the defective pattern 403 was −1 V, and the potential of the insulating film 402 was −2 V.

Figure 5:
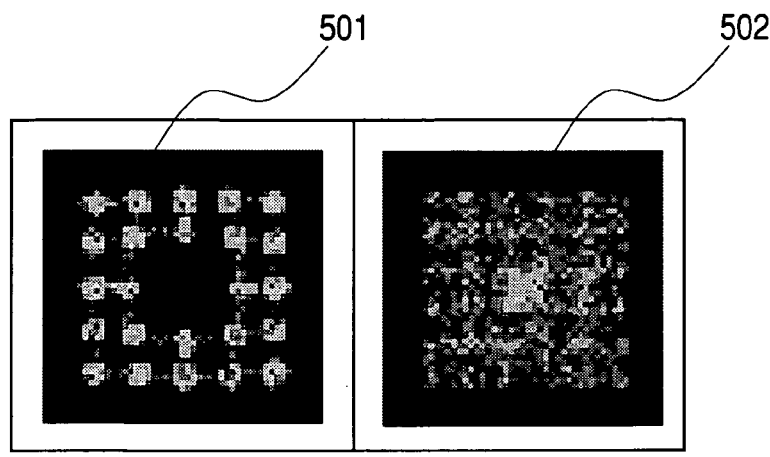
FIG. 5 is a view for a comparison between the states of images formed by mirror electrons.

FIG. 5 shows the results of obtaining images each formed on a fluorescence plate 14 by a mirror electron image forming optical system by varying the focus of the image forming system. As can be seen from an image 502 which is obtained by increasing the defocusing of the image forming system and shown in comparison with an image 501, an image of an extremely fine normal pattern has substantially disappeared and only the intensity of the image signal for the pattern defective portion is increased. This indicates that an image in which only the defect is emphasized can be formed by varying the focus of the objective lens 8 of the image forming optical system 102.

Figure 6:
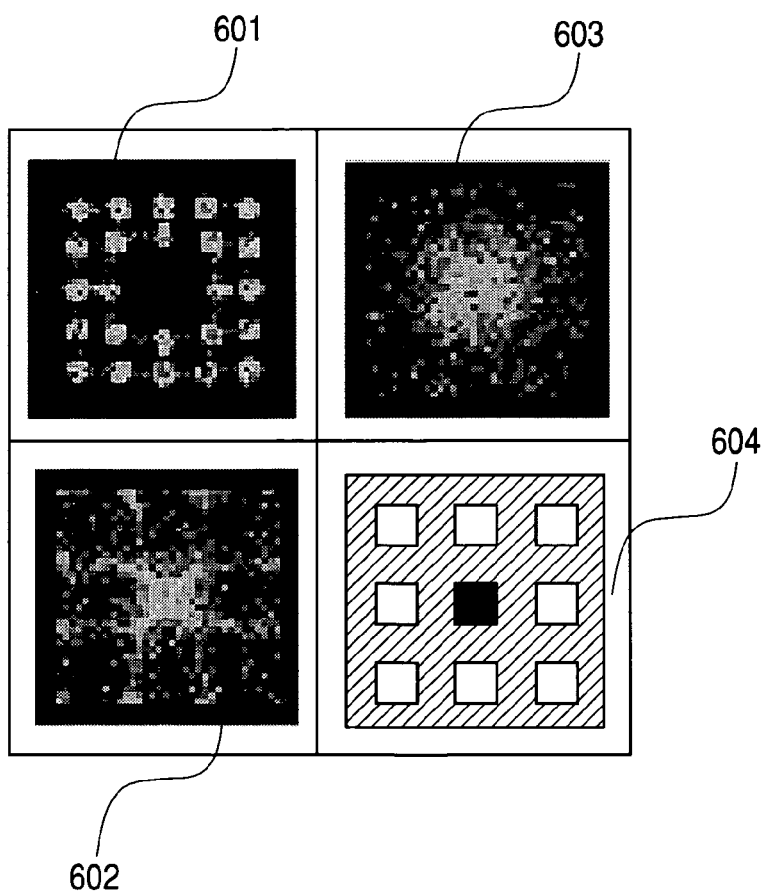
FIG. 6 is a view for a comparison between the states of images formed by mirror electrons.

FIG. 6 shows changes in images when the conditions for the electron beam irradiation system 101 are varied, not the conditions for the mirror electron image forming system 102. As shown in a pattern model 604, the drawing shows only the 3×3 arrangement portion at the center of the pattern model shown in FIG. 4. An image 602 was obtained by increasing the width (full width at half maximum) of the energy distribution of the irradiation electron beam compared with that of the irradiation electron beam used to form the image 601. On the other hand, an image 603 was obtained by reducing the degree of parallelness of the irradiation electron beam compared with that of the irradiation electron beam used to form the image 601. When the energy width of the irradiation electron beam is increased or the degree of parallelness of the irradiation electron beams is reduced by slightly converging or diverging an incident electron beam, a change with a short periodicity observed in a normal pattern does not appear in the image but a change with a periodicity larger than the pattern size formed by a distorted potential distribution resulting from a defect appears in the image.

To increase the width of the energy distribution of an irradiation electron beam, a chip having a tip with a small radius of curvature may be selected appropriately as the electron source 1 or a quantity of an extracted current may be increased appropriately by increasing an extraction voltage for the chip of the electron source 1. Alternatively, the crossing angle of the cross over 108 may be reduced appropriately by reducing the power of the condenser lens 2 and thereby shifting the position of the cross over 108 toward the sample. In either case, the interaction between electrons becomes more prominent and the width of the energy distribution can be increased. To lower the degree of parallelness of an irradiation electron beam, on the other hand, a voltage and a current supplied to the condenser lens 2, the EXB deflector 7 for aberration correction, and the like may be adjusted appropriately. By predetermining the combinations of the values of the supplied voltage and current in correspondence to the degrees of parallelness of an incident electron flux and tabulating them, the control unit 106 performs the detailed adjustment thereof through mere selection of the degree of parallelness by the user. Thus, by adjusting the electron source 1, the condenser lens 2, and the like as the components of the electron beam irradiation system 101, an image in which only a defect is emphasized can be formed.

In the sample room 103, the wafer 4 has been placed on the sample moving stage 9 and such a negative potential as to prevent the major part of the electron beam from colliding with the wafer 4 has been applied to the wafer 4 from the power source 11. An additional stage position measuring device 18 is provided in the sample moving stage 9 to precisely measure the position of the stage in real time. This is for acquiring an image while continuously moving the stage 9. For example, a laser interferometer is used for the stage position measuring device 18.

To precisely measure the height of the surface of the sample wafer 4, an optical sample height measuring device 19 is also mounted. For the optical sample height measuring device 19, a system can be used in which, e.g., light is obliquely incident upon the surface region of a wafer to be inspected and the height of the wafer surface is measured from a change in the position of the reflected light. In addition, an aligner 20 used to align the region to be inspected has also been provided. For example, an optical microscope, a laser interferometer, or the like is used as the aligner 20 which is used in aligning the moving direction of the sample moving stage 9 with respect to the orientation of patterns arranged on the wafer 4.

A description will be given next to a method for operating the sample moving stage 9. If a step-and-repeat system is adopted as a method for moving the stage 9, it takes a time of an order of milliseconds for the stage 9 to move in one step. So, the inspection time cannot be reduced because of settling time of the stage 9, even though image acquisition time is reduced by an improvement of the S/N ratio of an image. Accordingly, a continuous moving system in which the stage is constantly moving at a substantially equal speed was adopted as the method for moving the stage 9. This eliminates the constraint on the inspection time placed by the stage settling time. When the stage 9 is moving continuously, the stage 9 moves even during one shot which is a time required to form an image at the same place so that an irradiation position on the surface of the wafer changes disadvantageously. To prevent the change in irradiation position during one shot, the irradiation electron beam is caused to follow the movement of the stage 9 by an irradiation system deflector 21. The movement of the stage 9 and the deflection of the irradiation electron beam are controlled by controlling the stage controller 22 and deflector controller 23 of the control unit 106 by using a control calculator 24.

A description will be given next to the image detection unit 104. To detect an image, the fluorescence plate 14 for converting a mirror electron image to an optical image and the optical image detector element 16 are optically coupled by using the optical image transmission system 15. In the present embodiment, an optical fiber bundle is used as the optical image transmission system 15. The optical fiber bundle is composed of fine optical fibers which are equal in number to pixels and tied in a bundle. It is also possible to use an optical lens instead of the optical fiber bundle and cause an optical image on the fluorescence plate 14 to be formed on the photo-sensing surface of the optical image detector element 16 by using the optical lens. The optical image detector element 16 converts the optical image formed on the photo-sensing surface thereof to an electric image signal and outputs the electric image signal. As the optical image detector element 16, there can be used a CCD, an MCP (micro-channel plate), a photodiode, or the like. The resolution of the acquired image can be adjusted to be larger than the size of a pattern that should be judged for the presence or absence of a defect.

For a rectangular pattern with sides of, e.g., 70 nm, a resolution of 200 nm, which is about triple the side of 70 nm, is sufficient, as can be judged from the image 603 in FIG. 6 or the like. In the case of the present embodiment, if it is assumed that one pixel of the optical image detector element 16 is assigned to a region which is 200 nm square, a sufficient number of pixels assigned to the region irradiated with the irradiation electron beam, which is 50 μm square, is 250×250. If a plurality of channels for reading out pixel data is further provided, the fetching of the image data can be performed at an extremely high speed. Alternatively, a TDI sensor using a time-delay integration CCD may also be used.

The image processor 105 is composed of an image signal storage unit 25 and a defect judging unit 26. The image storage unit 25 acquires data on the deflection of the irradiation electron beam and data on the position of the stage from the control calculator 24 and stores image data in association with coordinate systems on the sample wafer. The image data shown as coordinates on the wafer is compared with the preset value by the defect judging unit 26 for the judgment of a defect. The coordinates and the signal intensity of a corresponding pixel are sent to the control calculator 24 and stored therein. The value for the comparison is set via the control calculator 24.

Operational instructions to the individual components of the apparatus and the operating conditions therefor are inputted and outputted via the control calculator 24 in the control unit 106. To the control calculator 24, various conditions including an acceleration voltage at the generation of an electron beam, the deflection width/speed of the electron beam, the moving speed of the sample stage, and the timing of latching an image signal from the image detector element have preliminarily been inputted. Upon receipt of a command from the control calculator 24, a correction signal is generated based on signals from the stage position measuring device 18 and the sample height measuring device 19 and sent to the objective lens power source 27 and the deflector controller 23 such that the electron beam constantly irradiates a proper position. Upon receipt of a command from the control calculator 29, the stage control system 22 controls the sample moving stage 8. The control calculator 24 may also be composed of a plurality of calculators sharing the function and coupled by an interface.

A description will be given next to an actual inspection procedure. First, the alignment between the sample stage and the wafer is carried out with an aligner 20. The wafer 4 has been placed on the stage 9 via an alignment adjustment stage 28. The correction of the wafer position, such as rotation, is performed by using the alignment adjustment stage 28, while checking an alignment situation by using the aligner 20 such that a circuit pattern on the surface of the wafer 4 is parallel or orthogonal to the moving direction of the stage. To perform the alignment operation, marking has preliminarily been performed with respect to the surface of the wafer. When the positional relationship between the wafer 4 and the sample stage 9 is determined, the positional relationship to the irradiation electron beam 109 is adjusted.

Since mirror electrons form an image even with respect to the projections and depressions of the surface, they were used. A mark composed of the projections and depressions is made on either of the wafer 4 and the sample stage 9 and an image is acquired from the mark by using the image forming optical system 102. This allows the determination of the positional relationship between the wafer 4 or the sample stage 9 and the irradiation electron beam 107.

When the setting of the foregoing inspection conditions is completed, an electron beam image of apart of an inspection target region of the surface of the sample wafer 4 is formed under exactly the same conditions as actual inspection conditions. Information on the brightness of the image which is dependent on the material and configuration of the inspection target region and the range of variations thereof are calculated and judgment conditions for judging whether or not a portion of the pattern lying in the target region is defective.

After the setting of the inspection target region and the defect judgment conditions is completed according to the foregoing procedure, then an actual inspection is started. During the inspection, the stage 9 with the sample wafer 4 placed thereon continuously moves at a given speed in a plane perpendicular to the irradiation electron beam 107. Meanwhile, the electron beam irradiates the same irradiated region of the surface of the wafer 4 for a given shot time during each shot. Since the stage 9 is moving continuously, the electron beam is deflected by the irradiation system deflector 21 to scan the sample wafer 4, while following the movement of the stage 9.

The region irradiated with the electron beam or the irradiation position is constantly monitored by using the stage position measuring device 18 provided in the stage 9, the sample height measuring device 19, and the like. The obtained monitor information is transferred to the control calculator 24 such that a detailed amount of displacement is recognized. The amount of displacement is corrected and feedbacked to the electro-optical system.

In addition, the surface height of the sample wafer 4 is measured in real time by using a mechanism other than the electron beam such that the focal distances of the objective lens 8 for irradiation with the electron beam and the image forming lens system are dynamically corrected. As an example of the mechanism other than the electron beam, the optical height measuring device 19 using a laser interference system, a system which measures a change in the position of reflected light, or the like can be listed. This allows a focused electron beam image to be formed constantly on the surface of the inspection target region. It is also possible to obviate the necessity to measure the surface height of the wafer 4 during an actual inspection by preliminarily measuring the warping of the wafer 4 prior to the inspection and correcting the foregoing focal distances based on the measurement data.

The electron beam is directed toward the surface of the wafer 4 and an enlarged optical image of the desired target inspection region (areal region) of the surface of the wafer 4 is formed on the scintillator 14 by using mirror electrons. The enlarged optical image is converted to an electric image signal by using the optical image detector element 16 (e.g., a CCD), which is fetched by the image processor 105. As described above, it has preliminarily been determined to which position of the sample wafer the fetched image corresponds. It can be calculated from the information on the position of the stage at the time of image acquisition, which is obtainable from the stage position measuring device 18, and from the information on the amount of deflection given to the irradiation system deflector 21 based on the positional relationship between the sample stage 9 and the irradiation electron beam 107. Each of images is stored in the storage unit 25 in conjunction with the obtained information on a location on the wafer surface. The image signal is latched by the defect judgment unit 26, which performs a defect judgment based on the already determined defect judgment conditions and sends, to the control calculator 24, the coordinates of the location on the wafer surface judged to be defective together with the image signal.

The inspection method and inspection apparatus thus far described have allowed the location of a pattern defect to be detected by forming an image reflecting information on the potential of the surface of the wafer 4 and comparing the image signal for the corresponding pattern region with the set threshold value. As a result, it becomes possible to perform an extremely high-speed inspection compared with an inspection performed in a conventional inspection apparatus using an electron beam.

Embodiment 2

In the first embodiment, the lowest permissible positional accuracy of defect detection has been suppressed to about triple the pattern size or less. To simply detect only the presence or absence of a defect, however, the present invention can be implemented with a simpler structure. In the present invention, what is obtainable as an image is a potential distribution distorted by a defect. Accordingly, there is no image in a normal portion and an image signal is intensified only in a defective portion. If the accuracy required of the location of a defect is not so high, the presence or absence of a defect can be monitored based on the intensity of a whole image instead of obtaining a 2-D intensity distribution of an image.

Figure 7:
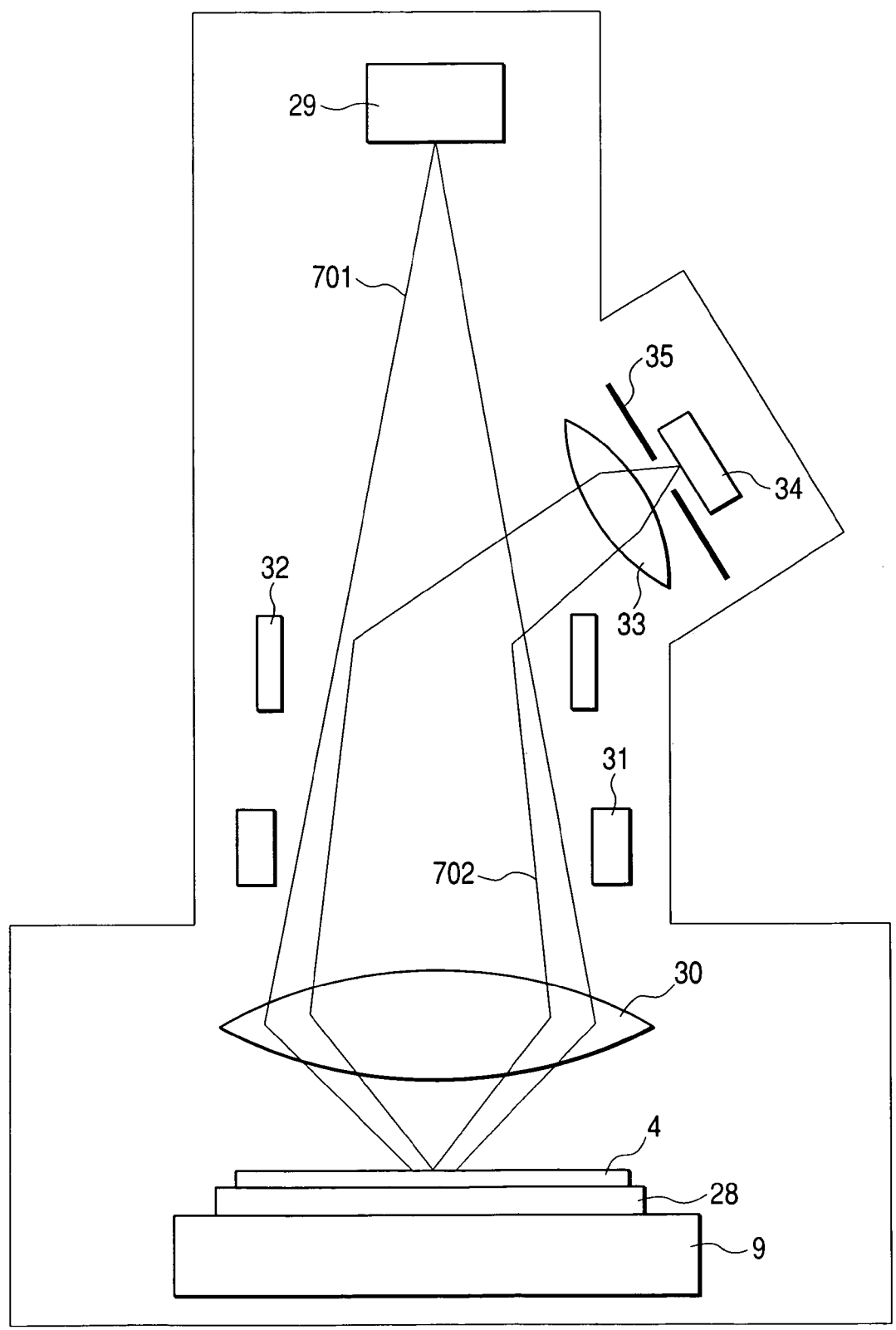
FIG. 7 is a view showing a schematic structure of an inspection apparatus as a second example of the present invention.

In the present embodiment, the size of the irradiated region for one shot is adjusted to about 5 μm and mirror electrons are signalized by using a simple detector for measuring only the magnitude of the intensity of a whole signal. The large difference from the first embodiment is that the signal intensity is measured at each of the 2-D positional coordinates of a CCD camera or the like and outputted as an image. In other words, the difference is that only the intensity of the mirror electrons as a whole is measured by using a CCD, MCP, photodiode, photomultiplier tube, or the like of the type without positional sensitivity, i.e., incapable of independently reading a signal for each of pixels, not that a mirror electron image is obtained by using a detector with positional sensitivity. FIG. 7 shows an embodiment obtained by modifying the structure of a normal SEM inspection apparatus. Since the present embodiment uses the same structure as used in the first embodiment except for the electro-optical system and the image detection system, the depiction of a vacuum exhaust system for maintaining a vacuum condition, equipment for controlling the apparatus, or the like has been omitted and only the portions associated with the electro-optical system are schematically shown.

In the same manner as in a normal SEM inspection apparatus, an irradiation electron beam 701 from an electron gun 29 is focused by the objective lens 30 onto the sample wafer 4. Although it is necessary in a normal SEM inspection to finely converge an electron beam for sufficient pattern recognition, the present embodiment adjusts the optical system to obtain a spot on the order of 5 μm on the surface of the sample wafer 4. For scanning with the electron beam, an electrostatic defector 31 is used. The electrostatic deflector 31 has been disposed on the focal plane of the objective lens 30 and an irradiation electron beam deflected by the electrostatic deflector 31 is applied perpendicularly to the sample for irradiation. A mirror electron beam reflected from the sample is deflected again in the same direction as the incident electron beam by the electrostatic deflector 31 so that the portion of the incident electron beam located above the deflector has a locus coincident with the locus of the mirror electron beam. The electrostatic deflector 31 need not necessarily be placed at the focal position of the objective lens 30. Two electrostatic deflectors may be used appropriately in combination such that the deflection point of the pair of electrostatic deflectors falls on the focal plane of the objective lens 30.

Between the electrostatic deflector 31 and the electron gun 29., an E×B deflector 32 is disposed as a separator. The sample wafer 4 is placed such that the electron beam applied in the same manner as in the first embodiment is reflected by a reverse electric field over the sample wafer 4. The reflected electron beam becomes mirror electrons 702 which are deviated from the optical axis of the irradiation electron beam by the E×B deflector 32 and focused by the image forming lens 33 to form an image on a detector 34. By using the electrostatic deflector 31 as a deflector for the irradiation electron beam, the electron beam incident on the detector 34 is constantly incident on the detector under the same optical conditions without receiving the influence of the electrostatic deflector 31. In addition, an aperture 35 is disposed before the detector 34 to prevent the electrons reflected from the portion of the sample wafer 4 without potential distortion from being incident on the detector 34.

The inspection method according to the present embodiment is substantially equivalent to that according to the first embodiment but it only compares an output value from the detector 34 with the preset threshold value for the judgment of the presence or absence of a defect. Accordingly, a defect judgment can be performed at an extremely high speed because it involves only a magnitude comparison between the output value and the set value. The position judged to have a defect has been determined from the degree of deflection of the irradiation electron beam 701 and the position of the sample stage 59 with the accuracy of the spot size (which is about 5 μm in the present embodiment) of the irradiation electron beam, which is sufficient to output a defect distribution over the sample wafer or the like.

According to the present embodiment, the presence or absence of a defect on the wafer can be inspected at an extremely high speed and a situation in which an electric defect occurs in a circuit pattern can be monitored without lowering the manufacturing throughput of a semiconductor device.

Embodiment 3

Figure 8:
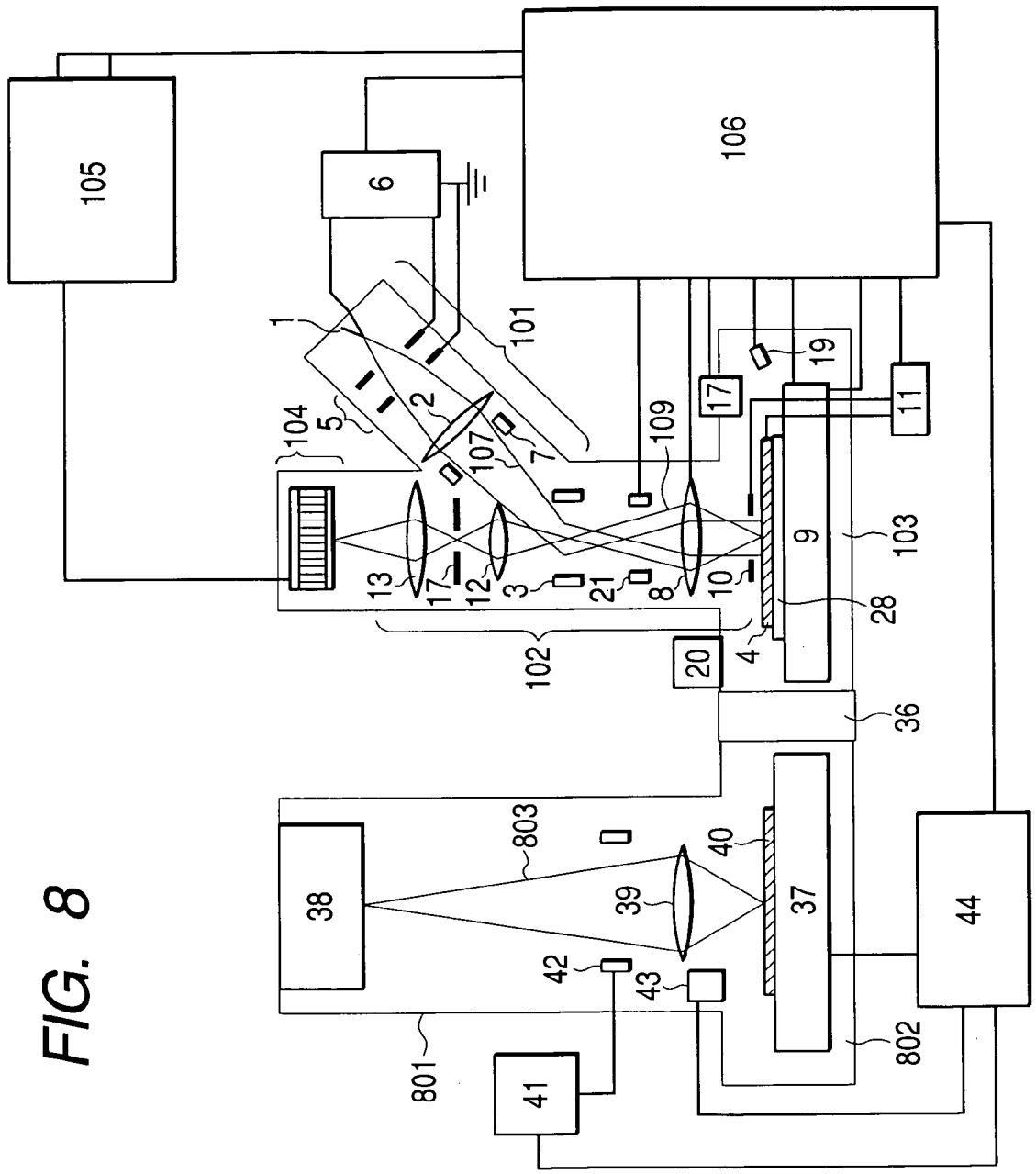
FIG. 8 is a view showing a schematic structure of an inspection apparatus as a third example of the present invention.

The present embodiment shows an example in which a second SEM tube 801 and the like are provided to enable a detailed defect inspection. FIG. 8 shows a structure thereof. Although the structure shown in the drawing is obtained by adding the SEM tube and the like to the first embodiment, the second embodiment may also be used instead of the first embodiment.

When particularly detailed observation should be performed with respect to a wafer on which the location of a defect has been determined according to the first embodiment (or the second embodiment), the wafer is transferred to the sample stage 37 under the SEM tube 801 by using a wafer transfer mechanism 36. The wafer transfer mechanism 36 comprises a mechanism capable of transferring the wafer from the sample room 103 to a sample room 802 without bringing the wafer out of the vacuum ambience. In the SEM tube 801, an electron beam 803 emitted from the electron gun 38 forms an extremely small spot on a transferred sample wafer 40 via the lens 39. Scanning with the electron beam 803 is performed by using a deflector 42 controlled by a deflection controller 41 to acquire an image of the wafer 40 from a signal from a secondary electron detector 43. At that time, it is also possible to take measures for improving observation quality by performing charging control, changing the position of secondary electron detection, or forming an image from secondary electrons generated upon the collision of the secondary electrons released from the wafer with another electrode.

When the wafer on which the location of a defect has been determined is transferred to the sample room 802, information on the location of the defect is transferred from the control unit 106 to a SEM control unit 44 so that the sample stage 37 and the deflector 42 are adjusted to locate the region to be scanned with the electron beam 803 at the location of the defect. It will easily be appreciated that the sample stage 37 is provided with an alignment mechanism for determining a reference for the transferred wafer 40 or the like such that the region to be scanned with the electron beam 803 is properly determined from the wafer positional information given by the control unit 106.

The image that has undergone SEM observation based on the defect positional information is fetched by the SEM control unit 44 where the outputting of the image to a monitor, a detailed judgment of the defect through a comparison with the defect information data, and the like are performed. The determination of an observation position, the detailed judgment of the defect, and the like may be performed either manually by an operator as an occasion demands or automatically by the SEM control unit 44.

It is also possible to inspect a defect on another wafer by using the first (or second) embodiment even during the detailed observation of the defect using the SEM tube 801, which prevents the lowering of the throughput of a defect inspection in a manufacturing line.

According to the present embodiment, detailed observation of a defect on a wafer can be performed without lowering the inspection throughput of the manufacturing line.

What is claimed is:

1. A pattern detect inspection method to irradiate an electron beam to a wafer formed with a circuit pattern, comprising:

charging the wafer to form a potential distribution in the vicinity of said circuit pattern;

adjusting a difference between an acceleration potential for the electron beam and the potential formed in the vicinity of said wafer into a value of which the incident electron beam is reflected without contacting the wafer;

monitoring a change pattern of said potential distribution; and detecting a fluctuation in potential intensity extending over a distance larger than a size of said circuit pattern or a repetition periodicity of said circuit pattern, which is included in the change pattern of the potential distribution to judge the presence or absence of an electric defect contained in said circuit pattern.

2. A pattern defect inspection method according to claim 1, wherein the change pattern of said potential distribution is detected by using a detector and a location of said electric defect is specified based on positional information of the detected fluctuation pattern.

3. A pattern defect inspection method according to claim 1, wherein the presence or absence of said electric defect is judged by comparing a potential intensity composing said detected variation with a specified threshold value.

4. A pattern defect inspection method according to claim 1, further comprising:
 irradiating said wafer with a planar electron beam having a size larger than a size of the periodicity of the circuit pattern;
 detecting the reflected electron beam to form an image by using the electron beam;
 detecting, from the image, a fluctuation in an intensity of an image signal which varies over a distance larger than the size of said circuit pattern or the repetition periodicity of said circuit pattern;
 moving a region irradiated with said planar electron beam over said wafer, while comparing said detected image signal intensity with a preset threshold value, to determine the presence or absence of a defect in the circuit pattern on the sample wafer and a location thereof.

5. A pattern defect inspection method according to claim 4, wherein said reflected electron beam is detected by using a detector with positional sensitivity.

6. A pattern defect inspection method according to claim 4, wherein said reflected electron beam is selectively focused on a detector without positional sensitivity by using an image forming mechanism and a diaphragm and said reflected electron beam is detected by using the detector without positional sensitivity.

7. A pattern defect inspection method according to claim 4, wherein defocusing is performed with respect to said reflected electron beam and a fluctuation pattern of the image signal intensity which fluctuates over a distance larger than the size of said circuit pattern or the repetition periodicity of said circuit pattern is measured by detecting the defocused electron beam.

8. A pattern defect inspection method according to claim 4, wherein
 a degree of parallelness of the electron beam incident on said wafer is adjusted,
 the electron beam with the adjusted degree of parallelness is made incident on said wafer, and
 a reflected electron beam of the electron beam with the adjusted degree of parallelness is monitored such that a potential change at a surface of the sample which extends over a distance larger than a size of a configuration of said circuit pattern or the periodicity of said circuit pattern is monitored.

9. A pattern defect inspection method according to any one of claims 1-8, wherein said wafer is charged by irradiating the wafer with an electromagnetic wave ranging in wavelength from an ultraviolet ray to a soft X-ray prior to or simultaneously with a pattern defect inspection.

10. A pattern defect inspection apparatus that irradiates an electron beam to a wafer formed with a circuit pattern, comprising:
 a mechanism for charging the wafer;
 a mechanism for controlling a charged potential of the wafer to a level which allows the irradiation planar electron beam to be reflected in the vicinity of the wafer without contact with the wafer;
 a mechanism for monitoring a potential intensity in the vicinity of the charged wafer; and
 a mechanism for detecting, from a change in the monitored potential intensity, a change extending over a distance larger than a size of said circuit pattern or a repetition periodicity of said circuit pattern to judge the presence or absence of an electric defect in said circuit pattern.

11. A pattern defect inspection apparatus according to claim 10, wherein said mechanism for monitoring the potential intensity in the vicinity of the charged wafer comprises:
 a first electro-optical system for irradiating a surface of the wafer with an electron beam having a two-dimensional expansion from an electron source as a planar electron beam;
 wherein a size of the planar electron beam is larger than a size of a periodicity of the circuit pattern;
 a second electro-optical system for forming an image of the specularly reflected electron beam to form an enlarged image of a region irradiated with the electron beam;
 a mechanism for scanning the region irradiated with the planar electron beam over the wafer;
 an image signal detecting mechanism for converting the enlarged image to an electric image signal and detecting the electric image signal; and
 a signal processing mechanism for comparing an intensity of the detected image signal with a set threshold value to determine the presence or absence of a defect in the circuit pattern and a location thereof.

12. A pattern defect inspection apparatus according to claim 11, wherein said image signal detecting mechanism comprises:
 a detector with positional sensitivity.

13. A pattern defect inspection apparatus according to claim 11, wherein the second electro-optical system comprises a diaphragm and an image forming mechanism for selecting only the electron beam reflected by a potential distribution which changes over a distance larger than a size of the circuit pattern or a repetition periodicity of the circuit pattern, and
 the image signal detecting mechanism comprises a detector for detecting said selected electron beam without positional sensitivity.

14. A pattern defect inspection apparatus according to claim 11, wherein the mechanism for charging the wafer is a mechanism for emitting an electron beam for irradiation or a mechanism for emitting an electromagnetic wave for irradiation which ranges in wavelength from an ultraviolet ray to a soft X-ray.

\* \* \* \* \*